US007097855B1

(12) United States Patent
Ameer et al.

(10) Patent No.: US 7,097,855 B1
(45) Date of Patent: Aug. 29, 2006

(54) TRANSDERMAL THERMAL POLYMERIZATION

(75) Inventors: Guillermo A. Ameer, Cambridge, MA (US); Eric T. Crumpler, Boston, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/495,278

(22) Filed: Jan. 31, 2000

(51) Int. Cl.
*A61K 9/10* (2006.01)
*A61K 47/32* (2006.01)

(52) U.S. Cl. ............... 424/486; 424/487; 424/422; 424/423; 424/424; 424/425; 424/426; 424/428; 514/944

(58) Field of Classification Search ........... 424/486, 424/487, 9.411, 422–426, 428; 514/944
See application file for complete search history.

(56) References Cited

U.S. PATENT DOCUMENTS

| | | | |
|---|---|---|---|
| 3,997,497 A | 12/1976 | Itoh et al. ............. 260/46.5 G |
| 4,379,864 A | 4/1983 | Gallop et al. ............. 523/106 |
| 4,622,371 A | 11/1986 | McDaniel ............. 526/117 |
| 4,638,040 A | 1/1987 | Hammar ............. 526/245 |
| 4,789,547 A | 12/1988 | Song et al. ............. 424/449 |
| 4,938,763 A | 7/1990 | Dunn et al. ............. 604/891.1 |
| 5,278,201 A | 1/1994 | Dunn et al. ............. 523/113 |
| 5,278,202 A | 1/1994 | Dunn et al. ............. 523/113 |
| 5,340,849 A | 8/1994 | Dunn et al. ............. 523/113 |
| 5,410,016 A | 4/1995 | Hubbell et al. ............. 528/354 |
| 5,618,800 A | 4/1997 | Kabra et al. ............. 514/57 |
| 5,626,863 A | 5/1997 | Hubbell et al. ............. 424/426 |
| 5,702,717 A | 12/1997 | Cha et al. ............. 424/425 |
| 5,733,950 A | 3/1998 | Dunn et al. ............. 523/113 |
| 5,736,152 A | 4/1998 | Dunn ............. 424/426 |
| 5,739,176 A | 4/1998 | Dunn et al. ............. 523/113 |
| 5,741,542 A | 4/1998 | Williams et al. ............. 427/208.4 |
| 5,744,153 A | 4/1998 | Yewey et al. ............. 424/426 |
| 5,759,563 A | 6/1998 | Yewey et al. ............. 424/426 |
| 5,834,274 A | 11/1998 | Hubbell et al. ............. 435/177 |
| 5,843,743 A | 12/1998 | Hubbell et al. ............. 435/177 |
| 5,858,746 A | 1/1999 | Hubbell et al. ............. 435/177 |

FOREIGN PATENT DOCUMENTS

| | | |
|---|---|---|
| DE | 33 12 424 | 10/1984 |
| WO | WO 94/25080 | 11/1994 |

OTHER PUBLICATIONS

The International Search Report.
Hill-West et al., "Prevention of Postoperative Adhesions in the Rat by Situ Photopolymerization of Bioresorbable Hydrogel Barriers", Obstetrics & Gynecology, 83(1): 59-64, 1994.
Kathmann et al., "Water-Soluble Copolymers, 67. Polyelectrolytes of N-Vinylformamide with Sodium 3-Acrylamido-3-Methylbutanoate, Sodium 2-Acrylamido-2-Methylpropanesulfonate, and Sodium Acrylate: Synthesis and Characterization", *Macromolecules*, 29: 5268-5272, 1996.

(Continued)

*Primary Examiner*—Edward J. Webman
(74) *Attorney, Agent, or Firm*—Choate, Hall & Stewart LLP; Samuel Pasternack; C. Hunter Baker

(57) ABSTRACT

An invention for polymerizing or crosslinking a prepolymer using a water soluble, thermal polymerization initiator is disclosed. The prepolymer mixed with the initiator is injected or placed into an animal's body, and heat is applied over the site of the injection to polymerize the polymer. This transdermal thermal polymerization system can be used for drug delivery of bioactive agents in tissue engineering applications in which living cells are delivered.

23 Claims, 3 Drawing Sheets

OTHER PUBLICATIONS

U.S. Appl. No. 08/862,740, Langer et al.

Elisseeff, et al., "Transdermal Photopolymerization for Minimally Invasive Implantation" *Proc. Natl. Acad. Sci. USA* 96(6):3104-3107, 1999.

Langer, R. "1994 Whitaker Lecture: Polymers for Drug Delivery and Tissue Engineering" *Ann. Biomed Eng.* 23(2):101-111, 1995.

Peter, et al., "Polymer Concepts in Tissue Engineering" *J. Biomed. Mater. Res.* 43(4):422-427, 1998.

Potts, et al., "Transdermal Drug Delivery: Useful Paradigms" *J. Drug Target* 3(4):247-251, 1995.

Sims, et al., "Injectable Cartilage Using Polyethylene Oxide Polymer Substrates" *Plastic Reconstructive Surgery* 98:843-850, 1996.

Technical Information on VA-044, Wako Pure Chemical Industries, Ltd., Japan, 1-8.

Technical Information on VA-50, Wako Pure Chemical Industries, Ltd., Japan, 1-21.

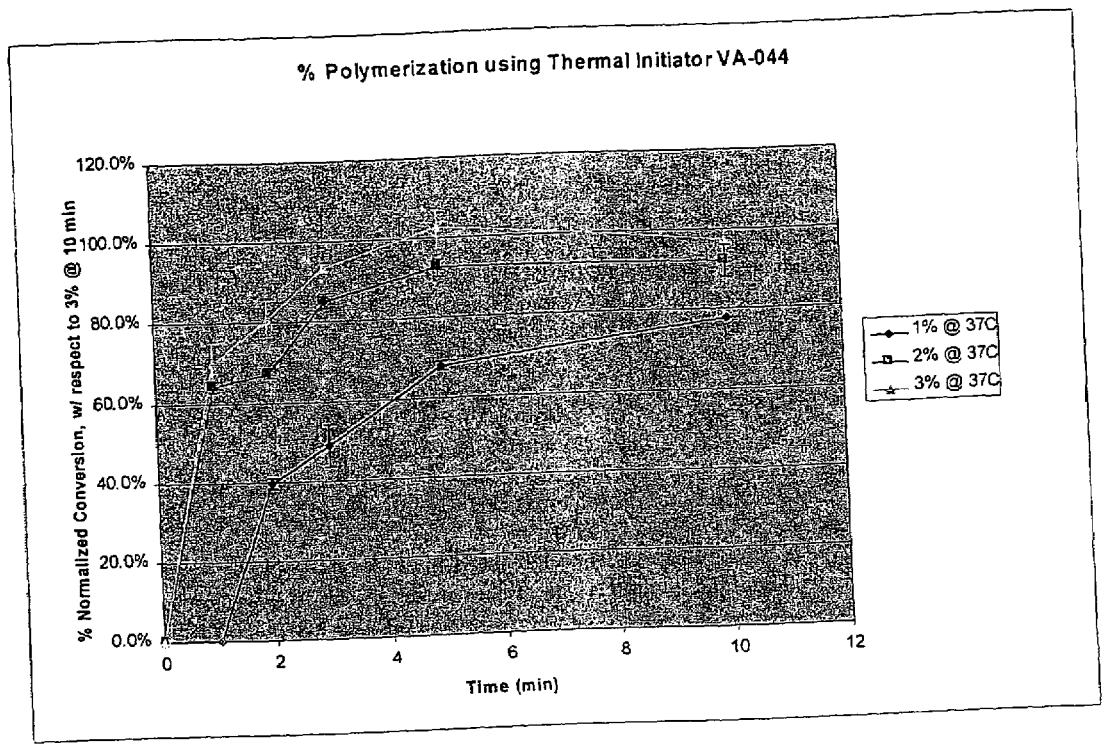
Figure 1. Gelation profile of PEGDM 20% wt/vol. At 37°C

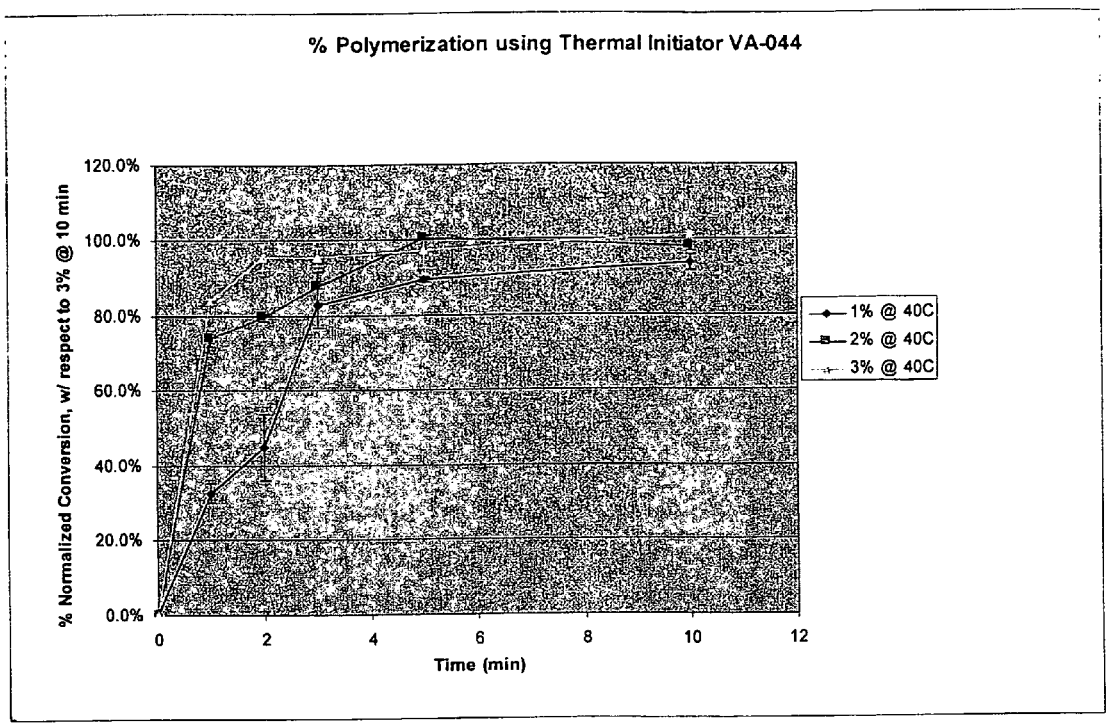
Figure 2. Gelation profile of PEGDM 20% wt/vol. At 40°C

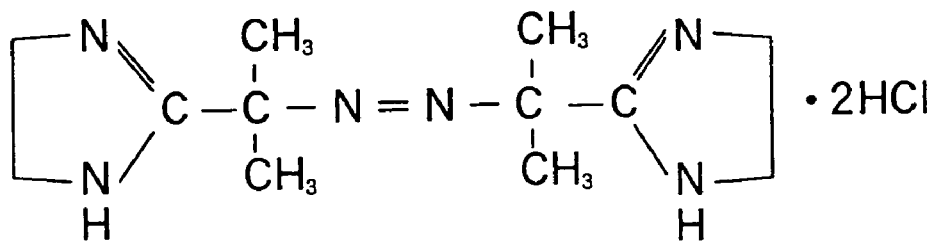
Molecular Weight : 323.33
Figure 3: Structure of 2,2'-azobis-(N,N'-dimethylene iso butyr amidine) di hydrochloride.

TRANSDERMAL THERMAL POLYMERIZATION

BACKGROUND OF THE INVENTION

The present invention relates to a minimally invasive system to achieve transdermal crosslinking or polymerization of hydrogels or other polymers for use in drug delivery or tissue engineering.

Fabricating polymers in situ provides many advantages over using preformed polymers for a variety of biomedical applications including drug delivery and tissue engineering. Prepolymerized liquid solution or moldable putties can be placed in an exact location and/or molded into complex shapes. Subsequent polymerization of the prepolymer yields a polymer of exactly the required shape and dimensions in the desired location. However, the formation of polymers in situ presents many challenges. Polymerization reactions which frequently occur by free radical reactions are quite adverse to physiological conditions including a narrow range of acceptable temperatures, requirement for nontoxic monomers and/or solvents, moist and oxygen-rich environments, and the need for rapid processing and clinically suitable rates of polymerization (Elisseeffet al., *Proc. Natl. Acad. Sci. USA* 96:3104–3107, 1999).

In the field of drug delivery, the implantation of a drug delivery device often involves a surgical procedure to place a formed drug-laden implant into a recipient's body at a desired site. These devices are usually made of a polymer impregnated with a bioactive agent to be delivered and are formed into shapes such as a sphere, cylinder, fibers, slab, or oval. The formed nature of these devices can lead to local irritation and inflammation at the site of implantation. As the polymer of the formed implant is degraded, the agent is gradually released in a controlled manner over an extended period of time. However, with the increased demand to minimize hospitalization stays and decrease patient morbidity, a drug delivery system which would require only a small incision or eliminate the need for a surgical procedure altogether would be very useful.

In the field of tissue engineering, many reconstructive plastic surgical procedures to correct deformities, whether traumatic or congenital, require invasive surgical techniques to place alloplastic prostheses. Griffith-Cima et al. in WO 94/25080 describe the use of injectable polysaccharide-cell compositions for delivering isolated cells by injection, which then form new tissue that is effective as a bulking agent. Sims et al. (*Plastic Reconstructive Surgery* 98:845, 1996) reported the formation of new cartilage from injected polyethylene oxide-cell suspensions and suggested that this technology would be useful in plastic surgery. A prosthesis which is formed in situ would eliminate the need for invasive surgical techniques.

A method of forming polymers in situ using photopolymerizaton of polymers which form semi-interpenetrating or interpenetrating polymer networks was described in U.S. Patent Application U.S. Ser. No. 08/862,740 by Langer et al. According to this application, one injects into a recipient's body a prepolymer solution which can be crosslinked, and then light is applied externally to the skin to crosslink the injected polymer. With the aid of a photoinitiator, the polymer will crosslink with an amount of light equivalent to 1–3 mW/cm$^2$ applied to the skin of nude mice. The polymer solution may consist of living cells for tissue engineering applications or may contain a bioactive agent for drug delivery applications. Disadvantages of using photopolymerization include exposing the patient and the living cells (in the case of tissue engineering) to potentially harmful ultraviolet rays and the difficulty of providing electromagnetic radiation to most sites within the body.

Other implantable delivery systems are known such as those disclosed by Dunn et al. in U.S. Pat. Nos. 5,739,176; 5,733,950; 5,340,849; 5,278,202; 5,278,201; and 4,938,763. In Dunn's system, a syringeable, in situ forming, solid biodegradable implant is formed in the recipient's body either by 1) the diffusion of a solvent, in which a polymer is dissolved, away from the polymer to produce the implant; or 2) the addition of a curing agent such as benzoyl peroxide or azobisisobutyronitrile to the prepolymer suspension prior to injection. A major drawback to this approach is the use of organic solvents such as N-methyl-2-pyrrolidone, dimethylformamide, and THF which can be toxic or irritating to body tissues. Another drawback is the rapid rate at which the curing agent polymerizes the implant even at room temperature. Therefore, the injection of the prepolymer suspension mixed with the curing agent must take place immediately after addition of the curing agent.

The instant invention avoids the use of organic solvents and ultraviolet radiation which can be harmful, and polymerization and formation of the implant does not take place at an appreciable rate until desired.

SUMMARY OF THE INVENTION

The present invention, in one aspect, is a method for polymerizing or crosslinking by transdermal thermal energy a perpolymer which has been placed in the body of an animal, and uses thereof. The material to be polymerized (prepolymer) contains unsaturated functional groups which can be cross linked or polymerized using a thermally activated initiator. For the purposes of this invention, the thermal initiator is preferably water soluble, initiates polymerization between 37 and 50° C., and is nontoxic. A suspension or solution of the prepolymer and initiator are placed subcutaneously using a syringe or through a small surgical incision. Once the suspension or solution is in place, a heat source is placed over the site, and thermal energy from the heat source causes the material to polymerize through the action of the thermal initiator. The thermal energy necessary to initiate the polymerization process can also be provided by the animal's own body heat, thereby eliminating the need for an external heat source.

Bioactive agents can be added to the suspension before placing it in the body of the animal, and polymerization in this case traps the bioactive agent in the polymer matrix at the site of the injection. Biodegradation of the polymer would then allow for a gradual release of the bioactive agent over an extended time period. In this way, the instant system is an implantable drug delivery system; however, no surgical procedure is necessary to place a preformed, drug laden implant inside the patient's body.

Other uses include tissue engineering. Living cells can be added to the prepolymer solution, and this suspension injected into the desired tissue. After polymerization, the cells are trapped in the polymer matrix and not able to migrate away from the site of interest. One potential advantage of transdermal thermal polymerization versus transdermal photopolymerization is the elimination of exposure of the living cells to potentially damaging ultraviolet rays. This embodiment of the invention may be used in orthopedic or reconstructive plastic surgery to correct traumatic and congenital deformities. The tissue engineering application may also be used in replacing or repairing cartilaginous surfaces.

In another aspect, the invention is a composition of prepolymer and initiator. In a preferred embodiment the prepolymer contains unsaturated functional groups which can be crosslinked or polymerized. In another preferred embodiment, the initiator is a thermally activated, water soluble initiator, which initiates polymerization between 37 and 50° C. In another embodiment, the composition may include a bioactive agent, and in another embodiment, the composition may include living cells.

In another aspect, the invention is as system for delivering a bioactive agent. The system comprises a prepolymer, and initiator, a bioactive agent, an apparatus for delivering the suspension into a recipient's body, and optionally a heating apparatus.

In another aspect, the invention is system for delivering living cells. The system comprises a prepolymer, an initiator, at least one living cell, an apparatus for delivering the suspension into a recipient's body and optionally a heating apparatus.

The safety and ease of using the instant invention make it desirable over earlier teachings in the prior art.

BRIEF DESCRIPTION OF THE DRAWINGS

FIG. 1 shows the gelation profile of polyethylene glycol dimethacrylate (PEGDM) (20% weight/volume) at 37° C.

FIG. 2 shows the gelation profile of polyethylene glycol dimethacrylate (PEGDM) (20% weight/volume) at 40° C.

FIG. 3 shows the chemical structure of 2,2'-azobis-(N,N'-dimethyleneisobutyramidine) dihydrochloride (AZODIA HCl).

DEFINITIONS

Animal refers to human as well as non-human animals. Non-human animals include mammals, birds, reptiles, amphibians, and fish. Preferably, the non-human animal is a mammal (i.e., a rodent, a mouse, a rat, a rabbit, a monkey, a dog, a cat, or a pig). An animal includes transgenic animals.

Biocompatible refers to material that is not toxic to the body, is not carcinogenic, and does not induce inflammation in body tissues.

Biodegradable refers to material that is degraded by normal bodily processes resulting in products which are readily disposable by the body and do not accumulate in the body.

Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (i.e., 2-aminoadenosine, 2-thiothymidine, inosine, pyrrolo-pyrimidine, 3-methyladenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (i.e., methylated bases), intercalated bases, modified sugars (i.e., 2'-hydroxylribose, 2'-fluororibose, ribose, 2'-deoxyribose, and hexose), or modified phosphate groups (i.e., phosphorothioates and 5'-N-phosphoramidite linkages).

Protein, peptide, or polypeptide refers to a polymer of amino acids, and these terms are used interchangeably. The polymer may include natural or unnatural amino acids. The protein or polypeptide may have been synthesized chemically in vitro or in vivo via natural or recombinant means. The protein or polypeptide may have post-translational modifications or may have been modified chemically to include phosphorylation, glycosylation, farnesylation, oxidation of thiols, etc.

Prepolymer or polymerizable material refers to any chemical compounds which can be cross linked or polymerized to form the desired polymer implant. These compounds may be monomers, partially polymerized material, uncrosslinked polymers, or hydrogels.

DETAILED DESCRIPTION OF THE INVENTION

The present invention provides methods, compositions, and systems for polymerizing or crosslinking a hydrogel or other polymer using thermal energy applied transdermally using an external heat source or provided by the animal's own body heat. In one preferred embodiment, the system is used to deliver bioactive agents or drugs. The agent or drug is preferably incorporated into the prepolymer mixture before injection and is retained in the polymer implant after polymerization. The polymer is slowly biodegraded over time to products which are excreted by the body.

In another embodiment, the system is used to deliver living cells to a particular site within the recipient's body. The cells are held in place while they reproduce to form a tissue or while they produce and secrete a desired substance such as a therapeutic peptide, hormone, or natural product. The polymer can then be metabolized by the body, and the products of the biodegradation process excreted leaving the tissue formed from the implant substantially the same as the natural tissue.

Polymers

Monomers, partially polymerized material, uncrosslinked polymers, and hydrogels can be polymerized in the instant invention. These prepolymers should include a substituent which leads to polymerization by a radical reaction initiated by a radical initiator. In a preferred embodiment, the material to be polymerized must possess unsaturated groups such as double bonds, triple bonds, or both, although double bonds (e.g. acroyl, methacroyl, allyl, vinyl groups) are preferable. The preferred polymerizable groups are acrylates, diacrylates, oligoacrylates, methacrylates, dimethacrylates, and oligomethacrylates. Acrylates are the most preferred active species polymerizable group. The material should also be nontoxic in its nonpolymerized as well as polymerized forms.

In a preferred embodiment, the polymer is biocompatible in the sense that the material is not toxic to the body, is not carcinogenic, and does not induce inflammation in body tissues.

In a preferred embodiment of the current invention, the polymer formed is both biocompatible and biodegradable. The polymer is biodegradable in the sense that it should degrade by bodily processes to products which are readily disposable by the body and do not accumulate in the body. Examples of biodegradable and biocompatible polymers of acrylic and methacrylic acids or esters include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), etc. Other polymers which can be used in the present invention include polyalkylenes such as polyethylene and polypropylene; polyarylalkylenes such as polystyrene; poly(alkylene glycols) such as poly(ethylene glycol); poly(alkylene oxides) such as poly(ethylene oxide); and poly(alkylene terephthalates) such as poly(ethylene terephthalate). Additionally, polyvinyl polymers can be used which include polyvinyl alcohols, polyvinyl ethers, polyvinyl esters, and polyvinyl halides. Exemplary polyvinyl polymers include poly(vinyl acetate), polyvinyl phenol, and polyvinylpyrrolidone. Mixtures of two or more of the above polymers could also be used in the present invention.

The polymer should have a half-life in a biological system on the order of weeks to months depending on the application. In certain preferred embodiments, the polymer might be chosen based on its characteristic half-life in a biological system.

In other preferred embodiments, the polymer might be chosen based on its ability to provide a substrate on which the desired cells can grow. In yet other preferred embodiments, the polymer might be chosen based on its ability to bind to or stabilize a particular bioactive agent which is to be delivered.

In other preferred embodiments, the pre-polymer is self-initiating. Self-initiating pre-polymers do not require a separate initiator to be added to start the polymerization/cross-linking reaction. One example of a self-initiating polymer is polystyrene. In a preferred embodiment, the pre-polymer may have functional groups attached to the backbone of the polymer, which initiate the polymerization process. In a particularly preferred embodiment, the thermal initiators discussed below are convalently attached to monomers or oligomers of the polymer to yield a self-initiating pre-polymer. The concentration of thermal initiator linked to the pre-polymer needed to effect polymerization might be different than the concentration of the thermal initiator when added separately.

Thermal Initiators

For the purposes of this invention, a thermal initiator is necessary to polymerize the polymerizable material (pre-polymer) using transdermal thermal energy. The initiator is preferably at a concentration of less than 10% by weight percent thermal initiator, more preferably less than 3% by weight percent thermal initiator, and, most preferably, between 2 and 0.01% by weight percent initiator. The precise concentration of the thermal initiator needed to effect polymerization would be known or could easily be determined by one of ordinary skill in the art. The thermal initiator should be water soluble and initiate polymerization in a temperature range not uncomfortable for the patient. A preferred temperature range is 37–50° C., and a particularly preferred range is 37–45° C. The thermal initiator should also be nontoxic or have limited toxicity.

In a preferred embodiment, the thermal initiator is an azo-based radical initiator. One preferred initiator of this class is 2,2'-azobis-(N,N'-dimethyleneisobutyramidine) dihydrochloride (AZODIA HCl) (FIG. 3) distributed by Wako Chemicals USA, Inc. This initiator is also known as 2,2'-azobis-[2-(2-imidazolin-2-yl) propane] dihydrochloride. This initiator has limited toxicity (LD50 (oral, rat) 2.8 and 3.2 g/kg for female and male, respectively), and it is extremely water soluble (35.2 g/100 g solvent at 20° C.).

Polymerization

The polymerization step is accomplished after the prepolymer suspension has been injected or placed into the desired site or tissue. The thermal initiator is preferably added to the prepolymer suspension before placement in the recipient's body; however, the initiator can be added by injection into the suspension after the suspension has been placed in the body. After the thermal initiator has been added to the prepolymer suspension, application of heat (thermal energy) will lead to polymerization. Any heat source can be used to provide the thermal energy in the polymerization step. Examples of heat sources include a heating pad, heat lamp, a light, water bath, hot water bottle, etc. The recipient's own body heat may also provide the heat necessary to initiate cross-linking or polymerization; however, the rate of the reaction may be slower, and consequently more thermal initiator may be required. Polymerization should occur within minutes once the heat source has been applied so as to limit diffusion of the prepolymer suspension and bioactive agent (if it had been added to the suspension) within the body.

Drug Delivery

A bioactive agent or drugs may be added to the polymerizable material anytime prior to polymerization. In a preferred embodiment, the bioactive agent is added before placing the suspension in the body at the target site. These bioactive agents may have therapeutic, prophylactic, or diagnostic activities. Examples of bioactive agents or drugs include peptide drugs, protein drugs, polynucleotides, oligonucleotides, antibiotics, anti-viral agents, steroidal agents, anti-inflammatory agents, anti-neoplastic agents, antigens, vaccines, antibodies, decongestants, antihypertensives, sedatives, birth control agents, progestational agents, anticholinergics, cholinergics, analgesics, anti-depressants, antipsychotics, β-adrenergic blocking agents, diuretics, cardiovascular active agents, non-steroidal anti-inflammatory agents, nutritional agents, etc.

Various forms of these drugs or bioactive agents may be used. The bioactive agent may be encapsulated in microspheres, microcapsules, or nanospheres. The agents may be in the form of uncharged molecules, molecular complexes, salts, ethers, esters, amides, etc. The bioactive agents may also be a prodrug which is biologically activated once inside the body.

Local delivery of the bioactive agent is achieved by the entrapment of the bioactive agent within the polymer during the transdermal polymerization process and the gradual release of the bioactive agent as the polymer is biologically degraded. In this preferred embodiment, the drug laden polymerized material acts as a drug depot over an extended period of time.

Tissue Engineering

Transdermal thermal polymerization can also be used in the field of tissue engineering. Living cells can be suspended in the polymerizable material which is injected into the desired tissue and polymerized with a source of heat. The cells are then retained in the polymerized matrix and can then divide or produce a bioactive agent (i.e., a peptide, steroid, protein, natural product, organic compound, etc.) locally.

The cells used in this embodiment can be obtained directly from a donor, from cell culture of cells from a donor, or from established cells lines. Preferably, the cells are of the same species as the animal to be treated and have the same immunological profile as the recipient. The cells may be obtained by a biopsy from the patient or a close relative, and then the cells may be grown in tissue culture using standard conditions as needed. In the most preferred embodiment, the cells are autologous; however, if the cells are likely to elicit an immune response, the recipient may need to be immunosuppressed using steroids or other immunosuppressant drugs such as cyclosporine.

Examples of cells which can be used in the tissue engineering embodiment of the instant invention include hepatocytes, myocytes, fibroblasts, chondrocytes, osteoblasts, pancreatic islet cells, neurons, and other cells acting primarily to synthesize and secrete materials, or to metabolize materials in the surrounding tissue.

In one preferred embodiment, the invention provides compositions to form cellular tissues and cartilaginous structures including polymerized material which will degrade and be removed to leave tissue or cartilage that is histologically, structurally, and chemically the same as naturally produced tissue or cartilage.

In another preferred embodiment, the cells to be implanted are genetically engineered. The cell type and source may be any of those listed above. The genetic engineering may allow the cells to secrete a bioactive agent not normally produced by the cell. The cells may also be engineered to correct a genetic defect.

These and other aspects of the present invention will be further appreciated upon consideration of the following Examples, which are intended to illustrate certain particular embodiments of the invention but are not intended to limit its scope, as defined by the claims.

EXAMPLES

Materials

Polethylene glycol dimethacrylate (PEGDM) (MW=3400) was obtained from Shearwater Polymers. Thermal initiator VA044 (2,2'-azobis-[N,N'-dimethyleneisobutyramidine] dihydrochloride) (FIG. 3) was obtained from WAKO Chemicals and stored at 4° C. in the dark.

Methods

Stock solutions of PEGDM were prepared at concentrations of 21, 22, and 23% weight/volume. 210, 220, and 230 mg of PEGDM were weighed out, and each was placed in a separate test tube. Distilled water was added to bring the total volume of the solution to 1 ml, and the solution was mixed well A stock solution of VA044 at a concentration of 25% weight/volume (0.25 mg/mL) was prepared. 31 mg of VA044 was weighed out, and distilled water was added to achieve a total volume of 125 µL. The solution was mixed well until it was clear.

In Vitro Determination of Polymerization Efficiency

Three samples were prepared that contained 20% PEGDM and 1, 2, and 3% weight/volume VA044 in 1.5 mL test tubes. By adding 2, 4, and 6 µL of the stock solution of VA044 (0.25 mg/µL) to 48, 46, and 44 µL of PEGDM solution (21, 22, and 23% weight/volume, respectively), pre-gel solutions with 1, 2, and 3% weight/volume of VA044 were obtained. The three samples were then thermally polymerized at 37° C. and 40° C. for 1, 2, 3, 5, and 10 minutes by incubation in a waterbath. The solid gel that formed was carefully removed from the test tube and weighed on a balance. The formation and weight of the solid gel was used as an indicator for the extent of polymerization. All samples gelled to completion after 10 minutes at both temperatures. The experimental data are shown in FIGS. 1 and 2.

Preliminary Safety and Efficacy Data on In Vivo Thermal Polymerization

Pre-gel polymer samples (100 µL) that contained rhodamine microspheres were injected subcutaneously into rats. A warm pad was placed over the injection site for 5 minutes. The injected liquid solidified, entrapping the rhodamine microspheres. No adverse reaction to the injection was observed macroscopically or histologically.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of drug delivery, the method comprising steps of:
   introducing into an animal's body (i) a polymerizable material (prepolymer), wherein the polymerizable material includes unsaturated carbon—carbon bonds,
   (ii) a thermal polymerization initiator selected from the group consisting of 2,2'-azobis-[N,N'-dimethyleneisobutyramidine] dihydrochloride and derivatives of 2,2'-azobis-[N,N'-dimethyleneisobutyramidine] dihydrochloride, and
   (iii) a diagnostic, therapeutic, or prophylactic agent; and
   applying thermal energy transdermally for a sufficient amount of time to polymerize or crosslink the said prepolymer, or allowing the pre-polymer to polymerize or crosslink using only the animal's own body heat as a thermal energy source.

2. The method of claim 1 wherein the step of providing an agent comprises providing a bioactive agent.

3. The method of claim 1 wherein the step of providing an agent comprises providing a protein.

4. The method of claim 1 wherein the step of providing an agent comprises providing a peptide.

5. The method of claim 1 wherein the step of providing an agent comprises providing a vaccine.

6. The method of claim 1 wherein the step of providing an agent comprises providing a polynucleotide.

7. The method of claim 1 wherein the step of providing an agent comprises providing an organic compound.

8. The method of claim 1 wherein the step of providing an agent comprises providing an agent within a microsphere.

9. The method of claim 1 wherein the polymerizable material is biodegradable before and after polymerization.

10. The method of claim 1 wherein the polymerizable material has unsaturated functional groups selected from the group consisting of double bonds and triple bonds.

11. The method of claim 1 wherein the polymerizable material has functional groups selected from the group consisting of acroyl, methacroyl, allyl, and vinyl.

12. The method of claim 1 wherein the polymerizable material is a hydrogel.

13. The method of claim 1 wherein the polymerizable material and thermal initiator are covalently linked together.

14. The method of claim 1 wherein the step of introducing comprises introducing the material and initiator under the skin, into a muscle, into a body cavity, into a potential space, or into an organ.

15. The method of claim 1 wherein the thermal polymerization initiator initiates polymerization between 37° C. and 45° C.

16. The method of claim 1 wherein the thermal polymerization initiator is water soluble.

17. The method of claim 1 wherein the thermal polymerization initiator has no toxicity in animals.

18. The method of claim 1 wherein the step of introducing comprises injecting said prepolymer and said initiator using a syringe.

19. The method of claim 1 wherein the step of introducing comprises placing said prepolymer and said initiator during a surgical procedure.

20. The method of claim 1 wherein the step of applying thermal energy comprises applying thermal energy from a heat source selected from the group consisting of a heating pad, a water bath, a hot water bottle, a heat lamp, and a light.

21. The method of claim 1, wherein the polymerizable material (prepolymer) is selected from the group consisting of acrylates, diacrylates, oligoacrylates, methacrylates, dimethacrylates, and oligomethacrylates.

22. The method of claim 1, wherein the polymerizable material (prepolymer) is an acrylate.

23. The method of claim 1, wherein the thermal polymerization initiator initiates polymerization between 37° C. and 50° C.

* * * * *